US010970089B2

(12) United States Patent
Kottler et al.

(10) Patent No.: US 10,970,089 B2
(45) Date of Patent: Apr. 6, 2021

(54) USER INTERFACE FOR DETERMINING REAL-TIME CHANGES TO CONTENT ENTERED INTO THE USER INTERFACE TO PROVIDE TO A CLASSIFIER PROGRAM AND RULES ENGINE TO GENERATE RESULTS FOR THE CONTENT

(71) Applicant: RADIOLOGY PARTNERS, INC., El Segundo, CA (US)

(72) Inventors: Nina Kottler, Rancho Santa Fe, CA (US); Thomas N. Tobias, Columbus, OH (US); Jason R. Mitsky, Portland, OR (US); Joyce Liang, Los Angeles, CA (US); Kelly Denney, Columbus, OH (US); Kevin Croxall, Lewis Center, OH (US); Telford Berkey, London, OH (US); Jai Salzwedel, Columbus, OH (US)

(73) Assignee: Radiology Partners, Inc., El Segundo, CA (US)

( * ) Notice: Subject to any disclaimer, the term of this patent is extended or adjusted under 35 U.S.C. 154(b) by 0 days.

(21) Appl. No.: 16/022,581

(22) Filed: Jun. 28, 2018

(65) Prior Publication Data

US 2020/0004561 A1    Jan. 2, 2020

(51) Int. Cl.
*G06N 5/04*     (2006.01)
*G06N 20/00*    (2019.01)
(Continued)

(52) U.S. Cl.
CPC ............ *G06F 9/451* (2018.02); *G06F 16/285* (2019.01); *G06F 40/174* (2020.01); *G06N 5/022* (2013.01); *G06N 5/046* (2013.01); *G06N 20/00* (2019.01)

(58) Field of Classification Search
CPC ...... G06F 9/451; G06F 16/285; G06F 17/243; G06F 40/174; G06F 9/285; G06N 5/046
See application file for complete search history.

(56) References Cited

U.S. PATENT DOCUMENTS 7,098,815 B1 *  8/2006  Samuels ................. H03M 7/30
                                                    341/51
7,801,721 B2    9/2010  Rosart et al.
(Continued)

OTHER PUBLICATIONS

Declaration Under 37 CFR 1.130 for U.S. Appl. No. 16/022,581, by Dr. N. Kottler, dated Aug. 30, 2018, 3 pp.
(Continued)

*Primary Examiner* — Ben M Rifkin
(74) *Attorney, Agent, or Firm* — Konrad Raynes Davda & Victor LLP; David W. Victor

(57) ABSTRACT

Provided are a computer program product, system, and method for determining real-time changes to content entered into a user interface to generate results for the content. In response to determining that entry of first content in a user input field rendered in a user interface is completed, the first content is provided to a classification program to classify into a first machine classification to provide to a rules engine to determine a first machine determined proposition. The first machine determined proposition is rendered in the user interface. A determination is made of second content in the user input field from the user that differs from the first content. The second content is provided to the classification program to classify into a second machine classification to provide to the rules engine to determine a second machine determined proposition rendered in the user interface with the second content.

10 Claims, 7 Drawing Sheets

(51) Int. Cl.
*G06N 5/02* (2006.01)
*G06F 9/451* (2018.01)
*G06F 16/28* (2019.01)
*G06F 40/174* (2020.01)

(56) References Cited

U.S. PATENT DOCUMENTS

| | | | |
|---|---|---|---|
| 9,043,901 B2 | 5/2015 | Chaudhri et al. | |
| 9,152,623 B2 | 10/2015 | Wroczy ski et al. | |
| 9,165,116 B2 | 10/2015 | Amies et al. | |
| 9,792,681 B2 | 10/2017 | Bryan et al. | |
| 9,916,420 B2 | 3/2018 | Cardoza et al. | |
| 2002/0078165 A1* | 6/2002 | Genty | G06F 16/9574 709/217 |
| 2007/0016442 A1* | 1/2007 | Stroup | G06Q 50/22 705/2 |
| 2007/0038037 A1* | 2/2007 | Fors | G06Q 50/24 600/300 |
| 2010/0108064 A1* | 5/2010 | Blackwell | A61M 16/024 128/204.21 |
| 2011/0112848 A1* | 5/2011 | Beraja | G06F 19/324 705/2 |
| 2012/0047105 A1* | 2/2012 | Saigal | G06N 5/048 706/52 |
| 2013/0253940 A1* | 9/2013 | Zziwa | G06Q 50/22 705/2 |
| 2013/0262364 A1 | 10/2013 | Verbeek | |
| 2017/0039529 A1 | 2/2017 | Reicher et al. | |
| 2018/0046764 A1 | 2/2018 | Katwala et al. | |
| 2018/0068406 A1 | 3/2018 | Van De Sande et al. | |
| 2018/0218737 A1 | 8/2018 | Herskovits | |

OTHER PUBLICATIONS

Declaration Under 37 CFR 1.130 for U.S. Appl. No. 16/022,581, by J.R. Mitsky, dated Aug. 30, 2018, 3 pp.
Denny, J.C., et al., "Comparing Content Coverage in Medical Curriculum to Trainee-Authored Clinical Notes", AMIA 2010 Symposium Proceedings, 5 pp.
Denny, J.C., et al., "Using Natural Language Processing to Provide Personalized Learning Opportunities from Trainee Clinical Notes", Journal of Biomedical Informatics, 56, 2015, 8 pp.
Herskovits, E.H., "RepScan: Real-Time Radiology Report Validation", SIIM 2016 Scientific Session, Posters & Demonstrations, Jun. 30, 2016, 2 pp.
Kim, D.C., et al., "Science to Practice: IT Solutions to Drive Standardized Report Recommendations for Abdominal Aortic Aneurysm Surveillance", Clinical Practice Management, © 2018 American College of Radiology, 5 pp. [Grace Period Disclosure].
Nuance Communications, Inc., "Nuance AI Marketplace for Developers", [online], © 2018, [Retrieved on Apr. 22, 2018], Retrieved from the Internet at <URL: https://aimarketplace.portal.azure-api.net/platform>, 2 pp.
Radoptimal, Inc., "Screenshots from RadOptimal, Inc. Website", Captured on Jun. 20, 2018, retrieved from Internet at <URL: https://radoptimal.com/demo.shtml>, 9 pp. [Grace Period Disclosure].
Statement Regarding Prior Disclosures by Another Who Obtained the Subject Matter From an Inventor or Joint Inventor, by David Victor, pp. 2, Sep. 5, 2018.

* cited by examiner

FIG. 2A

[Screenshot of document editor interface showing]

File Edit View Insert Format Tools Speech Help

Fields (5) | Addendum | Order Data

The Procedure was performed according to our departmental dose-optimization program which includes use of Automated Exposure Control, adjustment of the mA and/or kV according to patient size and/or use of iterative reconstruction technique.

FINDINGS:

[The lung bases are clear aside from atelectasis. No pericardial or pleural effusion.

The liver, spleen, kidneys, adrenal glands, gallbladder and atrophic pancreas are unremarkable. The stomach is massively distended. The duodenum is not dilated. No mass is seen. No ascites or small bowel obstruction. The colon is decompressed. Noninflamed diverticuli project of the distal colon. No free fluid is seen in the pelvis. Images through the pelvis are degraded by metallic artifact from the right hip replacement.

Vascular calcifications are present with aortic and coronary artery involvement. An infrarenal abdominal aortic aneurysm measures 5 x 5.1 cm in diameter and extends over 8.4 cm in length. The patient portion of the aortic lumen measures 3.3 x 1.6 cm. Vascular calcifications continue into both common iliac arteries. However, the aneurysm terminates at the level of the bifurcation.

The bones are osteopenic and degenerated. Posterior osteophytes along with facet hypertrophy causing. The central canal and neural foraminal stenosis within the lumbar spine. No acute fracture is seen. A total right hip arthroplasty is in place.]

IMPRESSION:

[5.1 cm infrarenal abdominal aortic aneurysm [Recommendation: Follow-up every 6 months and recommend vascular consultation. J Vasc Surg 2009 Oct:50(4 Suppl):S2-49.]

— 200
— 202 Observation Section
— 204
— 206
— 208 Impressions Section
— 210
— 220

FIG. 2B

AAA 6

4.0cm AAA. Recommend vascular consultation and annual follow-up. Reference: J Vasc Surg 2009 Oct:50(4 Suppl):S2-49.

— 222
— 224
— 226

| condition | AAA |
|---|---|
| sentence | SOFT TISSUES/SKULL: There is a 4 cm abdominal aortic aneurysm |
| size | 4.0cm |

FIG. 3

| User Entered Observations | Impressions | Machine Proposition |
|---|---|---|

— 300
— 302
— 304
— 306

Log File

FIG. 4

| Previous User Content Fingerprint | Current User Content Fingerprint |
|---|---|

User Content Information

— 400
— 402
— 404

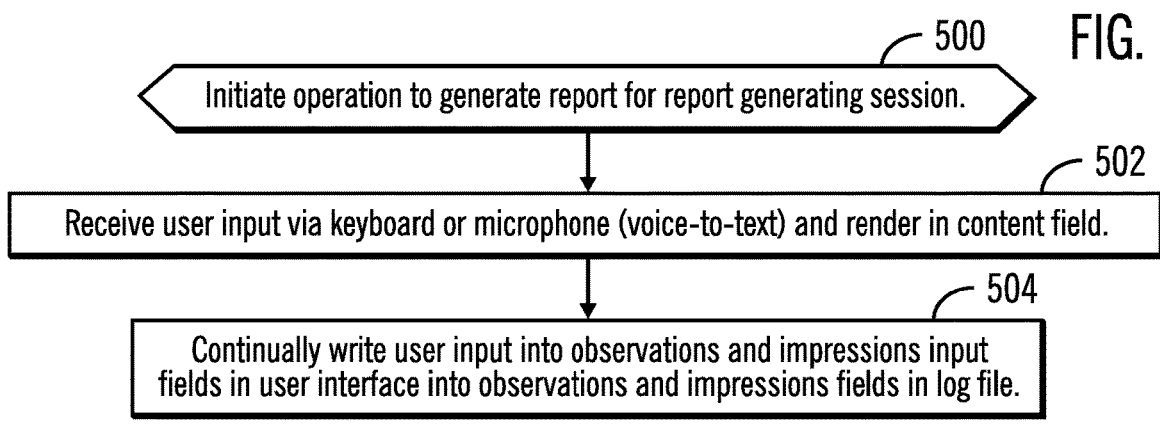
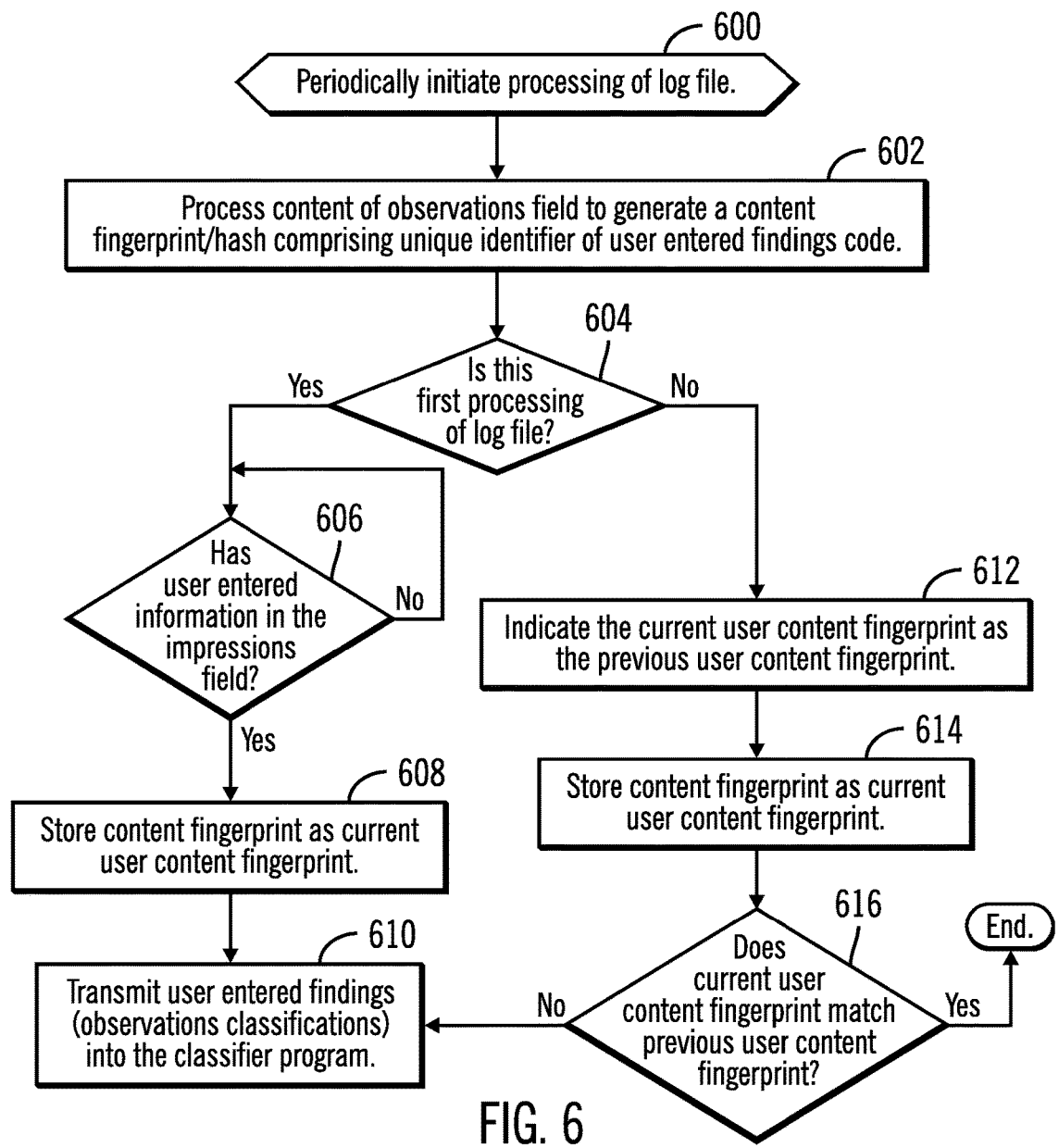

USER INTERFACE FOR DETERMINING REAL-TIME CHANGES TO CONTENT ENTERED INTO THE USER INTERFACE TO PROVIDE TO A CLASSIFIER PROGRAM AND RULES ENGINE TO GENERATE RESULTS FOR THE CONTENT

BACKGROUND OF THE INVENTION

1. Field of the Invention

The present invention relates to a computer program product, system, and method for a user interface for determining real-time changes to content entered into the user interface to provide to a classifier program and rules engine to generate results for the content

2. Description of the Related Art

Natural Language Processing (NLP) algorithms are used to classify information provided by a user via a computer user interface. In the medical field, NLP algorithms are used to process medical information from patient records or from clinician free form narration (audio or text) to extract clinical facts from the processed content. These extracted clinical facts may then be used to determine the completeness and accuracy of the gathered information and to alert the clinician of conditions to further explore and develop, to provide alerts, and to determine alternative hypothesis of diagnosis for the extracted facts. In this way, patient health records and doctor entered free form narration may be processed to provide diagnosis of patient conditions.

There is a need in the art for improved techniques for extracting information from a user interface in which user observations and findings are entered to process to determine results, actions and best practices for the extracted information.

SUMMARY

An embodiment may comprise a computer program product, system, and method for determining real-time changes to content entered into a user interface to provide to a classifier program and rules engine to generate results for the content. First content from a user in a user input field is rendered in a user interface. A determination is made that entry of the first content is completed. In response to determining that the entry of the first content is completed, the first content is provided to a classification program to classify the first content into a first machine classification to provide to a rules engine to apply a series of rules to determine a first machine determined proposition for the first machine classification. The first machine determined proposition is rendered in the user interface. A determination is made of second content in the user input field from the user that differs from the first content for which the first machine determined proposition is rendered. The second content is provided to the classification program to classify the first content into a second machine classification to provide to the rules engine to apply the series of rules to determine a second machine determined proposition for the second machine classification. The second machine determined proposition is rendered in the user interface with the second content.

In a further embodiment, a first fingerprint is generated from the first content that uniquely identifies the first content. A second fingerprint from the second content that uniquely identifies the second content. A determination is made as to whether the first fingerprint differs from the second fingerprint, wherein the second content is provided to the classifier program in response to determining that the first fingerprint is different from the second fingerprint.

In a further embodiment, the user input field comprises a first user input field. Determining that the first content is completed comprises detecting user input into a second input field in the user interface.

In a further embodiment, the first and the second content comprise user entered findings. The classifier program classifies the user entered findings as a machine classification. The first and second machine determined propositions each comprise at least one of reference material, calculations, summary of information from other sources, best practices, related to the machine classification.

In a further embodiment, the user input field comprises a first user input field. The first and the second content comprises user entered observations. User input is received indicating a user classification of the user entered observations in a second user input field. The classifier program additionally receives the user classification in the second user input field with the user entered observations in the first user input field to process to determine the first and the second machine classifications to provide to the rules engine.

In a further embodiment, the user entered observations comprise medical observations of a patient, the user classification comprises a user diagnosis of the user entered observations, the first and the second machine classifications comprise clinical diagnoses based on at least one of the user entered medical observations and the user diagnosis, and the first and second machine determined propositions from the rules engine comprise first and second medical best practices based on applying a series of rules of the rules engine to the clinical diagnosis from the classifier program. The term "best practices" may refer to best practice recommendations, best recommendations, and other types of preferred or relevant recommendations or actions, etc., to take based on an observed condition or diagnosis.

In a further embodiment, an action user interface is rendered with the second machine determined proposition and an acceptance control to allow a user to accept or reject the second machine determined proposition. The second machine determined proposition is rendered in the user interface with the second content in response to receiving, via the acceptance control in the action user interface, indication that the user accepted the second machine determined proposition.

In a further embodiment, the second machine determined proposition is rendered in the user interface with the second content and indication that the second machine proposition was not accepted in response to receiving rejection of the rendered second machine determined proposition through the action user interface.

In a further embodiment, at least one of a preferred classification and a preferred proposition is received from the user rejecting the second machine determined proposition with the acceptance control. A message is sent with the at least one of the preferred classification and the preferred proposition to an interface program managing access to the classifier program and the rules engine. Including the preferred classification in the rules engine trains the classification program to produce the preferred classification based on the second content used to produce the second machine determined proposition. Including the preferred proposition and the preferred classification programs the rules engine to associate the preferred proposition with the preferred classification. Including the preferred proposition with no preferred classification programs the rules engine to associate the preferred proposition with the second machine classification used to determine the second machine determined proposition.

In a further embodiment, content entered into the user input field is written into a log file. Content from the user input field is saved in the log file as previously entered content. The log file is periodically processed by determining whether the content from the user input field written to the log file matches the previously entered content. The determining the second content differs from the first content comprises determining that the content from the user input field in the log file matches the previously entered content. Indication is made of the content from the user input field in the log file as the previously entered content. The content from the user input field in the log file is sent to the classification program in response to the content in the log file not matching the previously entered content to obtain a new result from the rules engine to provide real time updating of the new result in the user interface.

BRIEF DESCRIPTION OF THE DRAWINGS

FIG. 2a illustrates an embodiment of a user interface into which user findings are entered and results based on the findings are rendered.

FIG. 2b illustrates an embodiment of a user interface in which machine generated best practices are rendered to a user.

FIG. 3 illustrates an embodiment of a log file.

FIG. 4 illustrates an embodiment of user content information used to generate information in the user interface.

FIG. 5 illustrates an embodiment of operations to generate a report through the user interface.

FIG. 6 illustrates an embodiment of operations to periodically process a log file to determine content to transmit to a classifier program.

DETAILED DESCRIPTION

Figure 1:
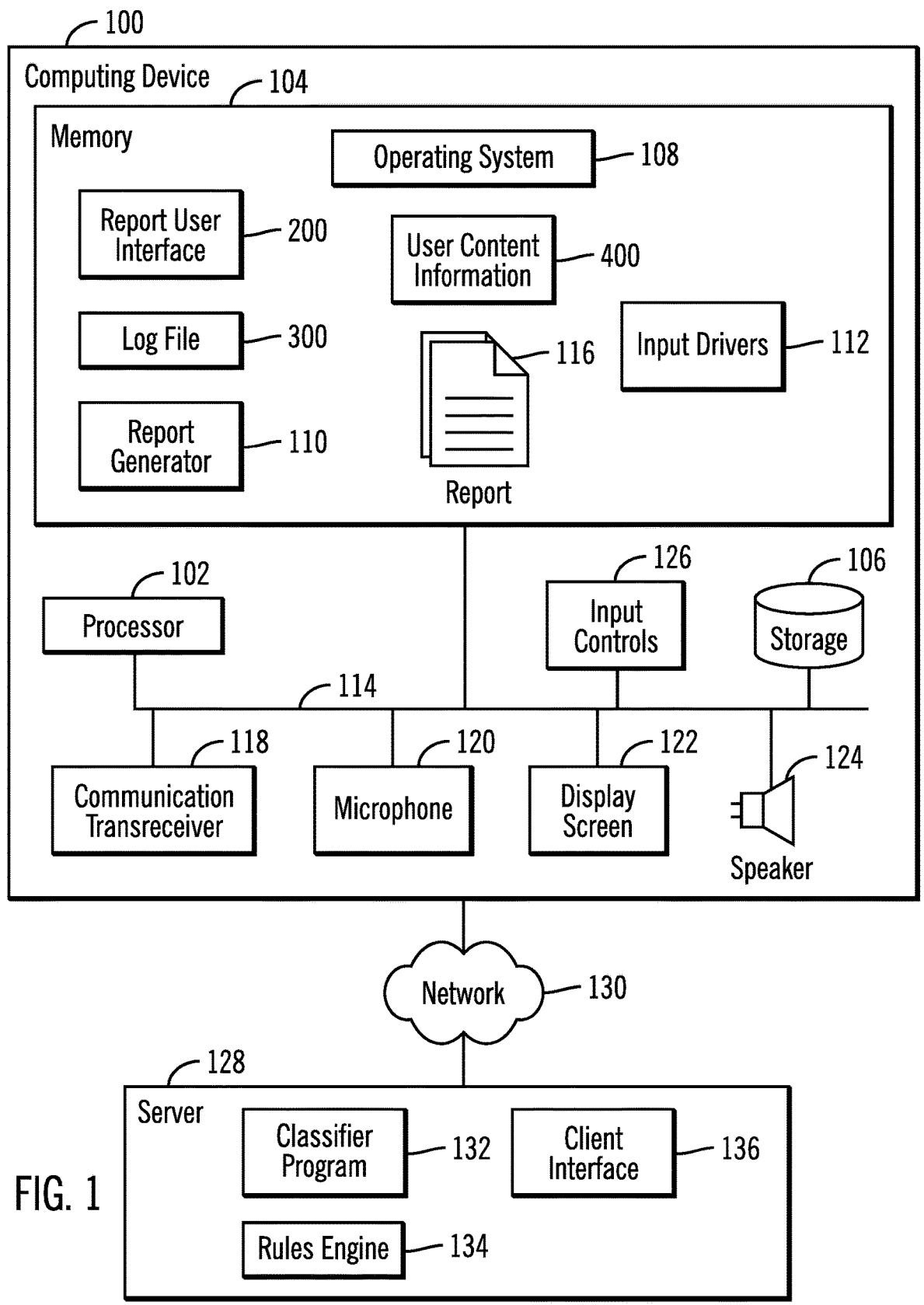
FIG. 1 illustrates an embodiment of a computing environment.

Described embodiments provide improvements to computer technology to provide real-time machine propositions for user content, including observations and user classification of the observations, entered into a user interface via an input device, such as a keyboard or voice-to-text device, where the machine propositions may include actions, recommendations, reference material, calculations, summary of information from other sources; best practices based on the findings, etc. For instance, a doctor or clinician may be entering observations and possibly a diagnosis of a condition, such as by observing the patient, lab test results, and medical images, and the clinician or doctor may want to be immediately informed of the relevant best practices based on the observed findings. Further, the clinician or doctor may want to see changes to the recommendations based on changes the clinician or doctor makes to the findings entered into a medical report rendered in a user interface to provide real-time feedback on such changes. Further, other types of professionals wanting to obtain recommended actions or best practices for observed findings, such as engineers analyzing a physical structure, device, manufacturing process, etc., or repair technicians may want to be informed real-time of the actions or best practices to take based on real-time entry of findings and observations and modifications to the findings.

Described embodiments provide improvements to the computer technology for determining real-time entry or changes to inputted content, such as user entered observations and classifications, entered into a user interface to process and present to a program, such as a machine learning classifier program and rules engine, to provide for real-time feedback when making changes to the inputted observations. In described embodiments, when first content, such as user inputted observations, is entered in the user interface, a determination is made when entry of the first content is completed. In response to entry of the first content, the first content is provided to a classification program to classify the first content into a first machine classification to provide to a rules engine to apply a series of rules to determine a first machine determined proposition for the first machine classification. The first machine determined proposition is rendered in the user interface. A determination is then made of second content in a user input field from the user, such as user entered observations, that differs from the first content for which the first machine determined proposition is rendered. The second content is provided to the classification program to classify the second content into a second machine classification to provide to the rules engine to apply the series of rules to determine a second machine determined proposition for the second machine classification. The second machine determined proposition is rendered in the user interface with the second content.

Further embodiments provide improvements to computer technology to determine changes to the user entered content, such as observations and classifications, entered into the user interface to provide to the classifier program to provide real time-feedback on actions to take based on the user entered findings. Content entered in to the user input field is written into a log file and content from the user input field in the log file is saved as previously entered content. To provide for real time feedback and real-time machine determined propositions based on changes to the user content entered into the user input field, the log file is periodically processed to determine whether the content from the user input field written to the log file matches the previously entered content. The determining that current entered content differs from the previously entered and processed content comprises determining that the content from the user input field in the log file matches the previously entered content. Content from the user input field in the log file is indicated as the previously entered content. The content from the user input field in the log file is sent to the classification program in response to the content in the log file not matching the previously entered content to obtain a new result from the rules engine to provide real time updating of the new result in the user interface.

In certain embodiments, the user entered observations may apply to processing user entered medical observations of patient data, observation of the patient conditions and attributes, digital images, and physical samples, such as biopsies and bodily fluid samples, to provide real-time feedback of best practices and recommendations to the user entered medical observations. Upon determining changes in the user entered findings, such as observations and classifications, the new inputted observations may be sent to a classifier program to determine from the user entered medical observations a predefined machine classification, such as a clinical diagnosis or recognized condition, to provide to a rules engine. The rules engine determines medical best practices based on applying a series of rules from the rules engine to the machine classification. The best practices and/or reference material, recommendations, calculations, summary of information from other sources, actions and other relevant information may then be immediately returned to render in the user interface to provide immediate feedback, such as for best practices and changes to best practices for user entered observations.

FIG. 1 illustrates an embodiment of a computing environment in which embodiments are implemented. A computing device 100 includes a processor 102, a main memory 104, and a storage 106. The main memory 104 includes various program components including an operating system 108, a report user interface 200, a report generator 110 to generate the report user interface 200, and input drivers 112 to interact with components connected on a bus 114. The memory 104 further includes a log file 300 in which content entered in the report user interface 200 is written, user content information 400 having information on content a user has entered in the report user interface 200, and a report 116 that may be generated from the content entered in the report user interface 200. The report user interface 200 may be continually displayed waiting to take action in response to user input.

The bus interface 114 may connect the processor 102, main memory 104, a communication transceiver 118 to communicate (via wireless communication or a wired connection) with external devices, including a network, such as the Internet, a cellular network, etc.; a microphone 120 to transmit and receive sound for the personal computing device 100; a display screen 122 to render display output to a user of the personal computing device 100; a speaker 124 to generate sound output to the user; and input controls 126 such as buttons and other software or mechanical buttons, including a keyboard, to receive user input. The components connected on the bus 114 may communicate over one or more bus interfaces 114 and other electronic interfaces.

The computing device 100 may communicate with a server 128 over a network 130 to transmit user content or findings and observations entered into the report user interface 200 to a classifier program 132 in the server 128 that processes the received user content to generate a classification based on the user entered observation. For instance, if the user observations comprise observations and findings with respect to a medical examination, medical images (e.g., X-Ray or magnetic resonance imaging digital image (MM)), the classifier program 132 may produce machine classification, such as a diagnosis or description, of the user entered findings. In this way, the classifier program 132 presents relevant information based on user entered descriptions, such as a specified pathology. The classifier program 132 may implement a machine learning technique such as decision tree learning, association rule learning, neural network, inductive programming logic, support vector machines, Bayesian network, etc., to determine a classification based on content entered by the user in the report user interface 200, such as medical observations and findings.

In one embodiment, the classifier program 132 may comprise a machine learning program that is trained using a training set comprising previously generated reports that have been classified with a ground truth classification, and the classifier program 132 is trained to produce the ground truth classifications provided for the training set of reports. For instance, if the training set comprises doctor entered findings, such as findings based on an MM reading, then the provided ground truths would be doctor determined classifications or clinical diagnosis based on those findings. The classifier program 132 would then be trained with those findings to produce the clinical diagnosis assigned to those findings and observations. The rules engine 134 would then take that machine classification, such as a clinical diagnosis, and determine a proposition, such as a result, action or best practices based on the classification using a decision tree or table that associates specific courses of action or results with the classification outputted from the classifier program 132. For instance, if the output of the classifier program 132 comprises a clinical diagnosis, then the rules engine 134 would determine the best practices to treat a clinical diagnosis outputted from the classifier program 132, such as a drug therapy, surgical treatment, further testing, further follow-up visit, etc. In this way, the rules engine 134 may provide a proposition, such as an action or best practices, reference material, calculations, summary of information from other systems, etc., for each possible classified diagnosis output from the classifier program 132.

In one embodiment, the findings may comprise a size of an observed condition on a patient, such as a size of an abdominal aortic aneurysms (AAA), observed features, such as size, shape, etc., of an incidental thyroid nodule, ovarian cyst, non-incidental thyroid nodule, enlarged thyroid, simple ovarian cyst, etc. The rules engine 134 may specify particular best practices given different sizes of the AAA, such as recommended follow-ups after so many years or a follow-up and an additional vascular consultation. In certain embodiments, the content is provided to the classifier program 132 in response to the radiologist adding text to the impressions section 206.

The server 128 may also include a rules engine 134 providing a decision tree of rules to map received predefined machine classifications outputted from the classifier program 132 to produce a machine determined proposition based on the outputted machine classification, such as a result or action to take based on the classification. For instance, if the machine classification from the classifier program 132 comprises a clinical diagnosis recognized by the rules engine 134, then the rules engine 134 may map that recognized clinical diagnosis to a best practices course of action to address that clinical diagnosis, such drug therapy, surgery, further testing, follow-up visit, etc. The server 128 may further include a client interface 136 to interface and manage communications with client systems to receive application calls from the report generator 110 operating in multiple client computing devices 100, such as at different facilities, companies or places of business. In alternative embodiments, the client interface 136 may receive application calls from another component. An advantage of having the rules engine 134 separate from the classifier program 132 is that the rules engine 134 may be independently updated to provide new results, actions or best practices for the classified condition or diagnosis outputted from the classifier program 132.

The network 130 may comprise one or more networks including Local Area Networks (LAN), Storage Area Networks (SAN), Wide Area Network (WAN), peer-to-peer network, wireless network, the Internet, etc.

The computing device 100 may store program components and corresponding data, such as 108, 110, 112, 116, 200, 300 in a non-volatile storage 106, which may comprise one or more storage devices known in the art, such as a solid state storage device (SSD) comprised of solid state electronics, NAND storage cells, EEPROM (Electrically Erasable Programmable Read-Only Memory), flash memory, flash disk, Random Access Memory (RAM) drive, storage-class memory (SCM), Phase Change Memory (PCM), resistive random access memory (RRAM), spin transfer torque memory (STM-RAM), conductive bridging RAM (CBRAM), magnetic hard disk drive, optical disk, tape, etc. The storage devices may further be configured into an array of devices, such as Just a Bunch of Disks (JBOD), Direct Access Storage Device (DASD), Redundant Array of Independent Disks (RAID) array, virtualization device, etc. Further, the storage devices may comprise heterogeneous storage devices from different vendors or from the same vendor.

The memory 104 may comprise a suitable volatile or non-volatile memory devices, including those described above.

Generally, program modules, such as the program components 108, 110, 112, 200, 132, 134, 136 may comprise routines, programs, objects, components, logic, data structures, and so on that perform particular tasks or implement particular abstract data types. The program components and hardware devices of the computing device 100 and server 128 of FIG. 1 may be implemented in one or more computer systems, where if they are implemented in multiple computer systems, then the computer systems may communicate over a network.

The program components 108, 110, 112, 200 may be accessed by the processor 102 from the memory 104 to execute. Alternatively, some or all of the program components 108, 110, 112, 200, 132, 134, 136 may be implemented in separate hardware devices, such as Application Specific Integrated Circuit (ASIC) hardware devices.

The functions described as performed by the programs 108, 110, 112, 200, 132, 134, 136 may be implemented as program code in fewer program modules than shown or implemented as program code throughout a greater number of program modules than shown.

FIG. 1 shows the classifier program 132 and rules engine 134 implemented in a server 128 over a network 130. In an alternative embodiment, the classifier program 132 and rules engine 134 may be implemented in the computing device 100 including the report generator 110 and user interface 200. In further embodiments, the server 128 may comprise a cloud server providing cloud services for classifying user input with the classifier program 132 and determining a course of action or best practices for the classification of the classifier program 132.

FIG. 2a illustrates an embodiment of a user interface 200 in which a user may input data, and includes a observations section 202 in which a user may enter observations about an entity being diagnosed, such as a person, device, natural phenomena. The user may describe observations from an image or video, direct observation of a phenomena, etc. The user may further enter impressions 206, such as classifications and conclusions, in an impressions section 208 providing a classification of the observations, such as a condition, medical diagnosis, natural phenomena, state of a device, etc. The impressions section 208 may further render an action, solution, best practices, etc. 210 produced by the classifier program 132 and rules engine 134. The classifier program 132 may receive the user entered observations 302 and optionally the user classification 304, such as a diagnosis or conclusion of observations the user inters in field 206 of the user interface 200, and classify into a machine classification, such as a clinical diagnosis, category, etc., which is then provided to the rules engine 134 to determine a machine proposition, e.g., result, action, recommendation, best practices, etc. 210 to render in the user interface 200 concerning the user machine classified findings.

In certain embodiments, the report user interface 200 may be continually displayed waiting to take action in response to user input into the impressions section 208 providing the classification.

FIG. 2b illustrates an embodiment of an alert user interface 220, which may be displayed as a dialog box or pop-up alert, rendered on top of the user interface 200, that alerts the user of a machine determined proposition 222 based on the user entered content and findings 204 and 206, which may comprise a machine determined best practices from the rules engine 134 based on the user entered observations and classification, or diagnosis, of the observations. The user may select an accept selection control 224 to cause the machine determined best practices 222 to be entered into field 210 of the user interface 200 to accept the machine generated best practices from the rules engine 134. The user may also select a reject selection control 226 to reject the machine determined best practices. The user may enter the machine determined best practices 22 into the report user interface 200 by voice command, copy and paste from the field 222 in the alert user interface 220 into the best practices field 210 of the user interface 200, or click a button, such as 224 and 226 to cause the automatic insertion of the best practices recommendation in the field 222 of the alert user interface 220 into the user interface 200, such as into field 210.

The user interface 200 provides improvements to computer technology for rendering machine generated results, such as from a machine learning classifier program 132 and rules engine 134, by, in real-time, providing user entered observations 204 to the classifier program 132 and rules engine 134 to allow immediate computation of new machine propositions based on user entered findings, which include new observations 204 and user entered classifications 206, to immediately display in real-time the machine propositions 210, such as recommended actions, best practices, actions, calculations, reference material, summarized information from other sources, etc., in the user interface 200 as they are being entered in the observations 202 section. Further, at some point the observations 204, user entered classifications 206, and machine propositions 210 may be saved as a report 116 for later use. In further embodiments, other types of content and findings, in addition to or different from observations and classifications, may be entered in the user interface.

FIG. 3 illustrates an embodiment of a log file 300 to which content entered in the user interface 200 is written, including observations 302 entered in the observations section 202 of the user interface 200, such as exams and other patient related information; impressions 304 comprising the user entered classifications 206 entered in the impressions section 208; and the machine propositions 306 from the rules engine 134 from processing the machine classification produced by the classifier program 132, which is rendered as a machine determined proposition 210, e.g., best practices, etc. 210 in the impressions section 208.

FIG. 4 illustrates an embodiment of user content information 400 generated by the report generator 110 to determine when to transmit the observations 302 to the classifier program 132, and includes a previous user content fingerprint 402 comprising a unique fingerprint/hash code calculated from a previous state of the user entered impressions 304 and a current user content fingerprint 404 comprising a unique fingerprint/hash code calculated from a current state of the user entered impressions 304. The fingerprints 402 and 404 may be calculated using a fingerprinting algorithm to generate a unique code based on input, such as a fingerprinting method, or hash code generating algorithm.

FIG. 5 illustrates an embodiment of operations performed by the report generator 110 to render the report user interface 200, rendered on the display screen 122, to generate a report 116. Upon initiating (at block 500) an operation to generate a report 116 as part of a start of a report generations session, the report generator 110 receives (at block 502) user input via input controls 126, such as a keyboard mouse, touchscreen, or microphone 120 to renders in the report user interface 200. The report generator 110 continually writes (at block 504) user input entered into the observations 202 and impressions 208 sections into observations 302 and impressions (e.g., classifications) 304 fields, respectively, of the log file 300. In this way, the log file 300 is updated in real time with new information the user enters into the observations 202 and impressions 208 sections.

FIG. 6 illustrates an embodiment of operations performed by the report generator 110 to periodically process the log file 300 to implement real-time updating of the machine determined propositions 210 rendered in the user interface 200. The report generator 110 may periodically process the log file 300 after a time period, such as a fraction of a second or in response to the writing to the log file 300, etc. Upon processing (at block 600) the log file 300, the report generator 110 processes (at block 602) the content of the observations field 302 to generate a content fingerprint/hash code comprising a unique identifier of the user entered findings. If (at block 604) this is the first processing of the log file 300 for a report generation sessions, then the report generator 110 determines (at block 606) whether the user entered information in the impressions field 304, which may in certain embodiments signal that the user has completed entering the observations 302. In further implementations, the report generator 110 may continuously provide feedback entered through the user interface 200 without waiting for the user to input content into the impressions section 208. Other tests may be used to determine that the entering of the observations 304 has completed, such as selection of a button or user interface element. If (at block 606) a determination is made the user completed entering observations 304, then the content fingerprint calculated from the current observations 302 is stored (at block 608) as the current user content fingerprint 404. The user entered findings, such as observations 302 and impressions 304 are transmitted (at block 610) to the classifier program 132.

If (at block 604) this is not the first processing of the log file during a report generation session to generate a report, then the current user content fingerprint 404 is indicated (at block 614) as the previous user content fingerprint 402 and the generated content fingerprint is stored (at block 614) as the new current user content fingerprint 404. If (at block 616) the current 404 and previous 402 user content fingerprints do not match, then the user entered observations 304 has changed since last checked and the report generator 110 transmits the new user entered observations 302 to the classifier program 132 to generate new results. If (at block 616) the fingerprints 402 and 404 are not different, then control ends as there are no new impressions 304 to determine if there are new results, actions or best practices to render.

The embodiment of FIG. 6 provides improved computer technology to provide an immediate and real-time determination if new user observations 204 have been entered in the user interface 200 to provide for real-time updating of the results by immediately sending any changed user entered impressions 304 to the classifier program 132 and rules engine 134 to process. Any new results from the rules engine 134 may be displayed in the alert user interface 220 (FIG. 2B) in the determined proposition field 222, which the user may then cause to be inputted into the report 200. This allows for the immediate updating of the machine determined propositions 210 rendered in the alert user interface 220 based on new user entered findings, such as observations and/or impressions/classifications.

Figure 7:
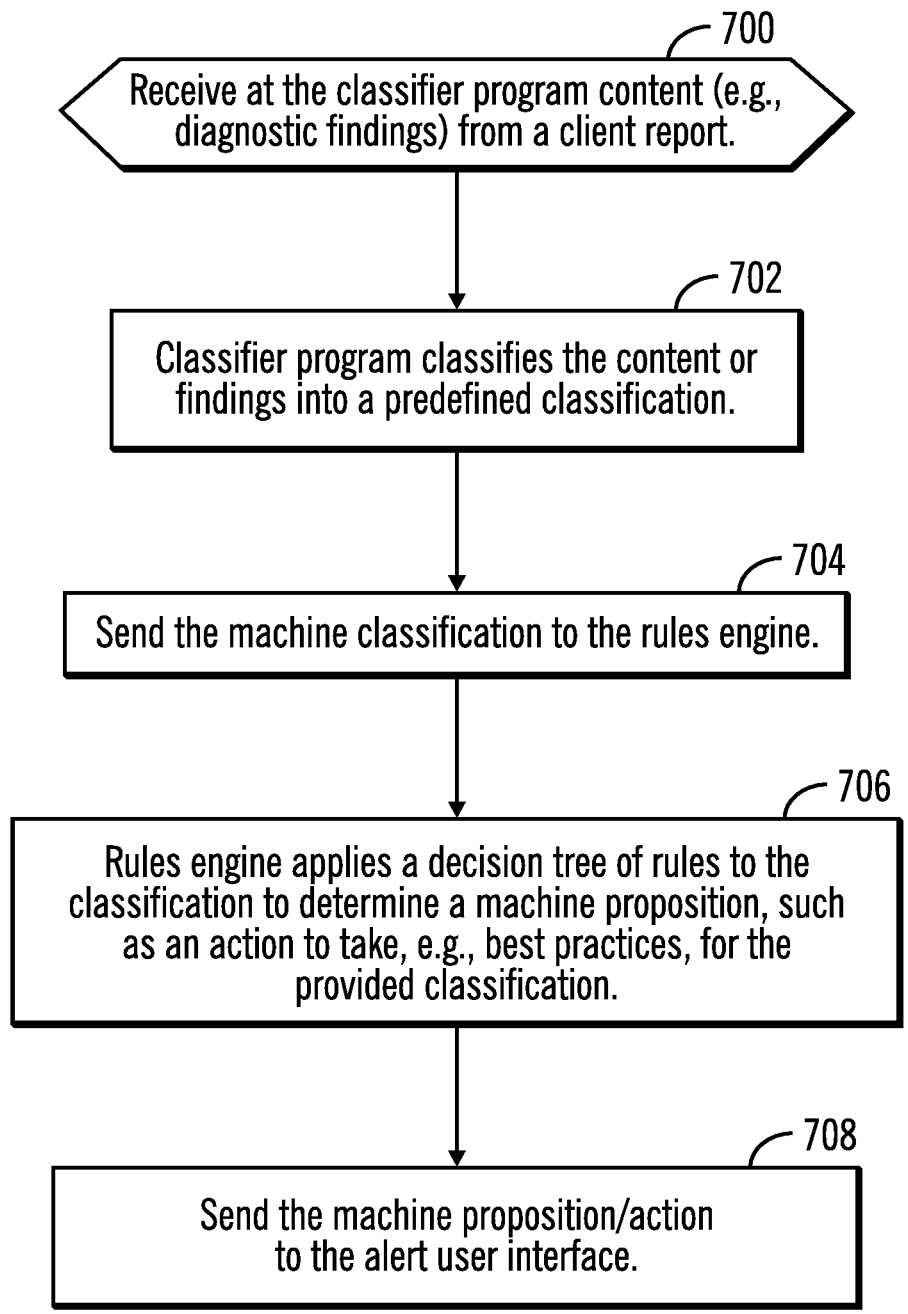
FIG. 7 illustrates an embodiment of operations for a classifier program and rules engine to generate results from findings entered in the user interface.

FIG. 7 illustrates an embodiment of operations performed by the classifier program 132 and the rules engine 134 to process observations 304 from the user to generate results. Upon receiving (at block 700) information from the user impressions 304 and other information, such as entered in observations 204, a classification of the observations 302, metadata, etc., the classifier program 132 classifies (at block 702) the entered information, e.g., impressions 304, etc., into a predefined machine classification, such as a clinical diagnosis or recognized condition. In additional embodiments, further information may be inputted into the classifier program 132, such as the user impressions 206, or user classification, and additional information from other sources. For instance, for medical diagnostics, in addition to receiving the user observations 204 and impressions 206, the classifier program 132 may receive medical lab results, information from other reports or sources, etc., all that may assist the classifier program 132 to produce a more accurate machine classification of the user entered findings, e.g., observations 302 and/or impressions 304. The classifier program 132 sends (at block 704) the determined machine classification to the rules engine 134.

Upon receiving the machine classification, the rules engine 134 applies (at block 706) a decision tree of rules to the machine classification to determine a machine proposition, such as an action to take, best practices, etc., for the provided classification. The determined result is returned (at block 708) to report generator 110 to render the result in the alert user interface 220 in field 222 to allow the user to add the determined result to the report. The report generator 110 or another program component may generate and manage the alert user interface 220.

With the embodiment of FIG. 7, user entered findings, such as observations and/or impressions, entered in real time are sent to the classifier program 132 and the rules engine 134 to provide immediate machine propositions, e.g., actions, best practices, etc. to return to the report generator 110 to immediately render the results in the alert user interface 220, such as field 222. This enables to the user to see in real-time the changes in the results, actions or best practices resulting from entering new findings, and determine whether to have them entered into the report being generated.

Figure 8:
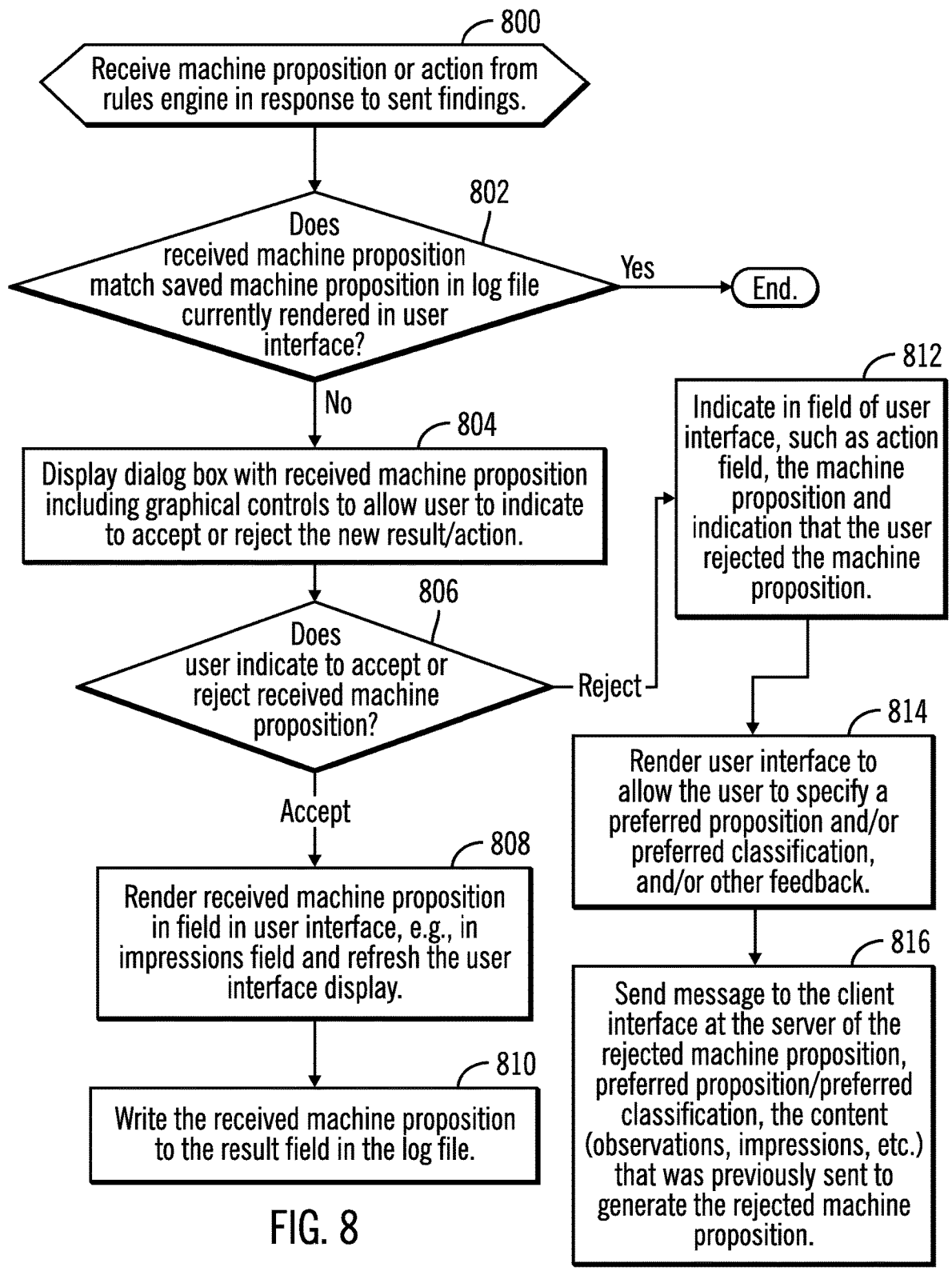
FIG. 8 illustrates an embodiment of operations to process results from the rules engine to render in the user interface.

FIG. 8 illustrates an embodiment of operations performed by the report generator 110 to process results received from the rules engine 134. Upon receiving (at block 800) a result, recommendation or action from the rules engine 134 in response to the sent observations 302, the report generator 110 determines (at block 802) whether the received machine proposition matches the machine proposition 306 saved in the log file currently rendered in field 210 of the user interface 200. If (at block 802) there is a match, then the machine proposition has not changed due to the change in the findings, e.g., observations and impressions, and control ends. If (at block 802) there is not a match, meaning the machine proposition or suggested action has changed since the previous findings, then the report generator 110 displays (at block 804) a dialog box, such as the alert notification dialog box 220 in FIG. 2b, showing the received machine determined recommendations 222 and graphical controls 224, 226 to allow the user to accept or reject, respectively, the new result in the dialog box 220. If (at block 806) the user has indicated to accept the received machine proposition, by select the accept graphical control 224, then the report generator 110 renders (at block 808) the received machine proposition in the field 210 in the user interface, e.g., in impressions field 208 and refresh the user interface display 200 with the new machine proposition. In further embodiments, the user can also copy/paste or use a provided macro to move the machine proposition anywhere into the report.

The new machine proposition is written (at block 810) to the machine proposition field 306 in the log file 300. If (at block 806) the user rejects the received machine proposition, such as by selecting the reject graphical control 226, then the received machine proposition is indicated in a field of the user interface 220, such as the action field 210 that the user, and indication is also made that the user, such as radiologist, disagreed with the machine proposition, such as actions, recommendations, reference material, calculations, summary of information from other sources; best practices based on the findings, etc. A user interface is then rendered (at block 814) to allow the user to specify a preferred proposition, e.g., best practices, and/or a preferred classification based on the current content in the user interface 200, as well as additional user feedback or comments. Upon receiving the user input, the report generator 110 sends (at block 816) a message to the client interface 136 at the server 128 with information on the rejected machine proposition, preferred proposition/preferred classification, the content (observations, impressions, etc.) that was previously sent to generate the rejected machine determined proposition, and any other feedback.

With the embodiment of FIG. 8, machine determined propositions are provided real time in response to the recently sent findings. In response, the report generator 110 renders an alert notification dialog 200 to allow the user to review the results, such as machine determined propositions, actions to take, best practices for medical diagnosis, etc., and then determine whether to accept the machine proposition to include into the report or user interface 200 being generated. Further, described embodiments provide improved techniques for allowing the user to provide input on the rejected machine proposition to improve the calculations and operations of the classifier program 132 and rules engine 134 by providing a user preferred classification and/or preferred proposition based on the current content rendered in the user interface 200 to the server 128 to retrain the rules engine 134 and/or classifier program 132 to further optimize operations and results. Further, the rejected machine propositions may be entered into the log file 300.

Figure 9:
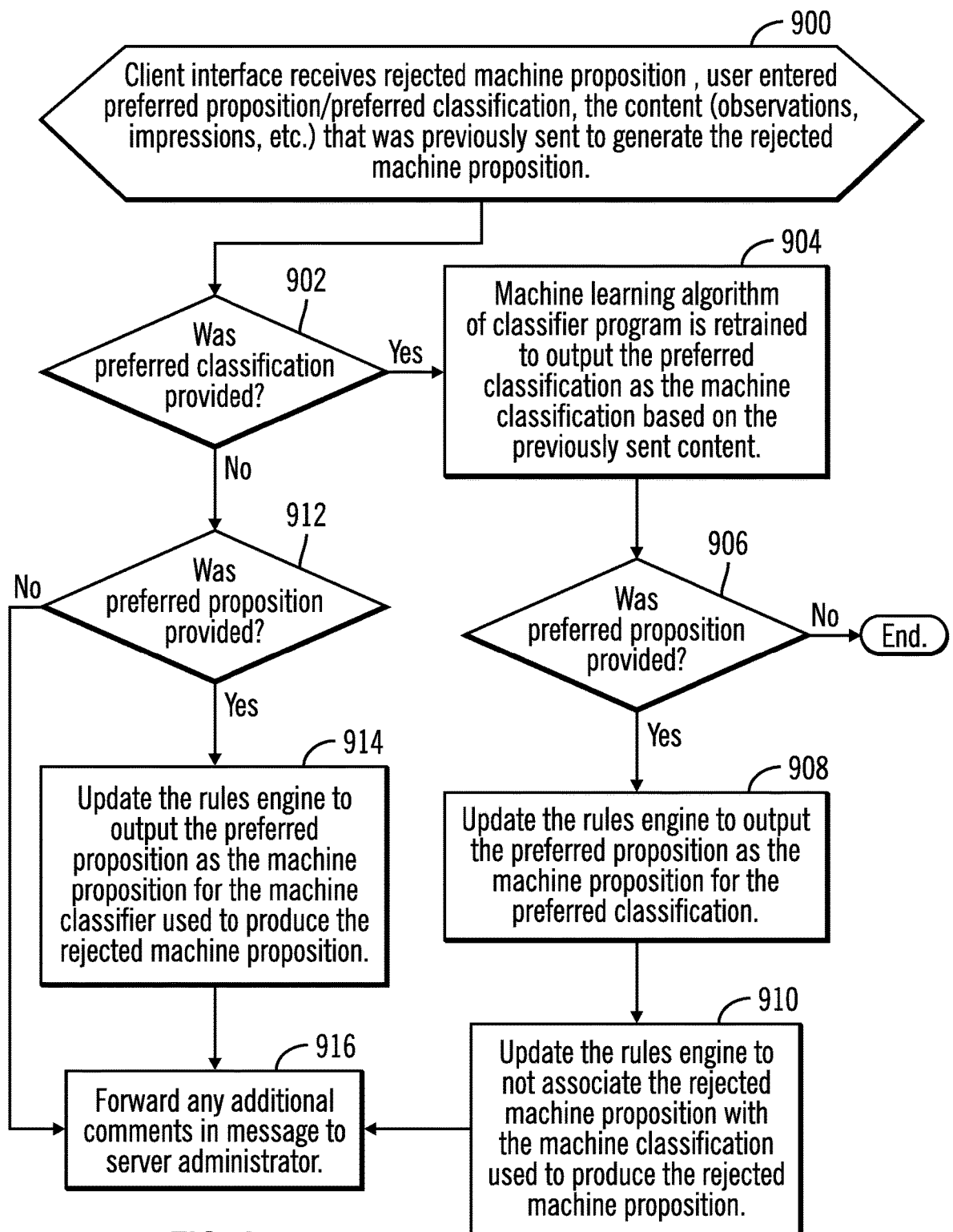
FIG. 9 illustrates an embodiment of operations performed to retrain the classifier program and/or rules engine based on a message rejecting a machine proposition.

FIG. 9 illustrates an embodiment of operations performed by the client interface 136, classifier program 132 and/or rules engine 134 to process a message sent from the report generator 110 where the user rejects the provided machine proposition. Upon receiving (at block 900) the message, including information on the rejected machine proposition, preferred proposition/preferred classification, the content (observations, impressions, etc.) that was previously sent to generate the rejected machine proposition, and any other feedback, if (at block 902) a preferred classification was provided, then the machine learning algorithm of the classifier program 132 is trained (at block 904) to output the preferred classification as the machine classification based on the previously sent content that resulted in the rejected machine proposition. If (at block 906) a preferred proposition is provided, then the rules engine 134 is updated (at block 908) to output the preferred proposition as the machine proposition for the preferred classification, which the classifier program 132 has been retrained to produce for the given current content. The rules engine 134 may further be updated (at block 910) to not associate the rejected machine proposition with the machine classification used to produce the rejected machine proposition, so as not to produce again the machine proposition that the user rejected given the current content, findings, impressions, observations, etc. in the user interface 200.

If (at block 902) a preferred classification was not provided and if (at block 912) a preferred proposition was provided, then the rules engine 134 is updated (at block 914) to output the preferred proposition as the machine proposition for the machine classifier used to produce the rejected machine proposition, so that the user suggested preferred proposition will be produced instead of the user rejected machine proposition for that machine classifier. From the no branch of block 912, block 914 or 910, any additional comments provided with the message are forward to a server administrator to consider for improving the performance of the classifier program 132 and/or rules engine 134.

The embodiment of FIG. 9 provides improved computer technology for retraining the classifier program 132 and/or rules engine 134 to produce user preferred output when the user rejects a machine proposition previously sent to allow continual improvement of the machine propositions produced for given content, such as improved actions, best practices, etc.

The present invention may be a system, a method, and/or a computer program product. The computer program product may include a computer readable storage medium (or media) having computer readable program instructions thereon for causing a processor to carry out aspects of the present invention.

The computer program product comprises a computer readable storage medium implemented using standard programming and/or engineering techniques to produce software, firmware, hardware, or any combination thereof. The described operations may be implemented as code or logic maintained in a "computer readable storage medium". The term "code" and "program code" as used herein refers to software program code, hardware logic, firmware, microcode, etc. The computer readable storage medium, as that term is used herein, includes a tangible element, including at least one of electronic circuitry, storage materials, a casing, a housing, a coating, hardware, and other suitable materials. A computer readable storage medium may comprise, but is not limited to, a magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), Solid State Devices (SSD), computer encoded and readable punch cards, etc. The computer readable storage medium may further comprise a hardware device implementing firmware, microcode, etc., such as in an integrated circuit chip, a programmable logic device, a Programmable Gate Array (PGA), field-programmable gate array (FPGA), Application Specific Integrated Circuit (ASIC), etc. A computer readable storage medium is not comprised solely of transmission signals and includes physical and tangible components. Those skilled in the art will recognize that many modifications may be made to this configuration without departing from the scope of the present invention, and that the article of manufacture may comprise suitable information bearing medium known in the art.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 10:
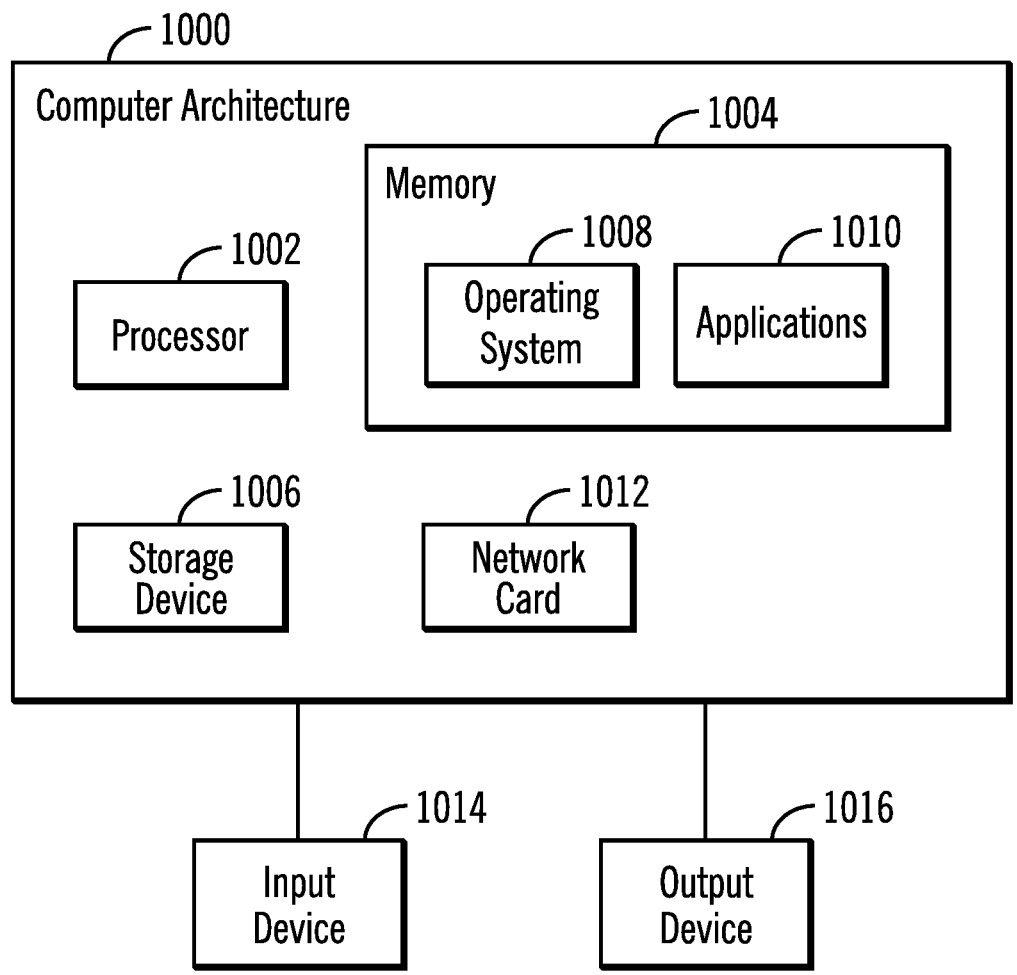
FIG. 10 illustrates a computing environment in which the components of FIG. 1 may be implemented

The computational components of FIG. 1, including the computer device 100 and the server 128, may be implemented in one or more computer systems, having a computer architecture as shown in FIG. 10, and including a processor 1002 (e.g., one or more microprocessors and cores), a memory 1004 (e.g., a volatile memory device), and storage 1006 (e.g., a non-volatile storage, such as magnetic disk drives, solid state devices (SSDs), optical disk drives, a tape drive, etc.). The storage 1006 may comprise an internal storage device or an attached or network accessible storage. Programs, including an operating system 1008 and applications 1010 stored in the storage 1006 are loaded into the memory 1004 and executed by the processor 1002. The applications 1010 may include the report user interface 200, report generator 110, input drivers 112, classifier program 132, rules engine 134, and client interface 136 and other program components described above. The architecture 1000 further includes a network card 1012 to enable communication with the network 16. An input device 1014 is used to provide user input to the processor 1002, and may include a keyboard, mouse, pen-stylus, microphone, touch sensitive display screen, or any other activation or input mechanism known in the art. An output device 1016, such as a display monitor, printer, storage, etc., is capable of rendering information transmitted from a graphics card or other component. The output device 1016 may render the GUIs described with respect to figures and the input device 1014 may be used to interact with the graphical controls and elements in the GUIs described above. The architecture 1000 may be implemented in any number of computing devices, such as a server, mainframe, desktop computer, laptop computer, hand held computer, tablet computer, personal digital assistant (PDA), telephony device, cell phone, etc.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims herein after appended.

What is claimed is:

1. A computer program product for processing user entered medical observations in a user interface to obtain a medical best practice recommendation, the computer program product comprising a computer readable storage medium having computer readable program code embodied therein that is executable to perform operations, the operations comprising:
   receiving a medical observation of a patient entered by a user in a first user input field in an observation section in a user interface page to render in the observation section;
   receiving content entered by the user in a second user input field in an impression section of the user interface page, comprising a classification or summary of the medical observation entered by the user in the observation section, to render in the impression section;
   determining whether entered content in the impression section has changed;
   in response to determining that the entered content in the impression section has changed, providing at least one of the medical observation in the observation section and the content in the impression section to a classification program, implementing a machine learning module, to classify into a machine classification comprising a medical finding based on at least one of the medical observation and the content in the impression section to provide to a rules engine, wherein the rules engine comprises a data structure that provides medical best practice recommendations for each of possible machine classifications outputted from the machine learning module, wherein the rules engine determines a medical best practice recommendation provided for the machine classification in the rules engine;
   generating an alert user interface rendered with respect to the user interface page, wherein the alert user interface renders the medical best practice recommendation from the rules engine and an accept selection control;
   receiving user selection of the accept selection control in the alert user interface; and
   rendering in a recommendation section of the user interface page the medical best practice recommendation rendered in the alert user interface to render with the observation section and the impression section in response to receiving the user selection of the accept selection control.

2. The computer program product of claim 1, wherein the classification program receives both the medical observation in the observation section and the classification or summary in the impression section in response to determining that the entered content in the impression section has changed.

3. The computer program product of claim 1, wherein the operations further comprise:
   storing in a log file a first fingerprint of first content entered in the impression section that uniquely identifies the first content;
   generating a second fingerprint of second content entered in the impression section that uniquely identifies the second content; and
   determining whether the first fingerprint in the log file differs from the second fingerprint, wherein the determining that the entered content in the impression section has changed comprises determining that the first fingerprint in the log file differs from the second fingerprint.

4. The computer program product of claim 3, wherein the operations further comprise:
   indicating the first fingerprint as a previous fingerprint in the log file and the second fingerprint as a current fingerprint in the log file;
   periodically processing the log file by:
      indicating the current fingerprint as the previous fingerprint;
      storing content in the impression section as the current fingerprint
      determining whether the current fingerprint calculated matches the previous fingerprint; and
      sending the current fingerprint to the classification program in response to the determining no matching to obtain a new medical best practice recommendation from the rules engine to provide real time updating of the new medical best practice recommendation in the user interface.

5. A system, comprising:
   a processor; and
   a computer readable storage medium having computer readable program code embodied that when executed by the processor performs operations, the operations comprising:
      receiving a medical observation of a patient entered by a user in a first user input field in an observation section in a user interface page to render in the observation section;
      rendering receiving content entered by the user in a second user input field in an impression section of the user interface page, comprising a classification or summary of the medical observation entered by the user in the observation section to render in the impression section by the user;
      determining whether entered content in the impression section has changed;
      in response to determining that the entered content in the impression section has changed, providing at least one of the medical observation in the observation section and the content in the impression section to a classification program, implementing a machine learning module, to classify into a machine classification comprising a medical finding, based on at least one of the medical observation and content of the impression section, to provide to a rules engine, wherein the rules engine comprises a data structure that provides medical best practice recommendations for each of possible machine classifications outputted from the machine learning module, wherein the rules engine determines a medical best practice recommendation provided for the machine classification in the rules engine;

generating an alert user interface rendered with respect to the user interface page, wherein the alert user interface renders the medical best practice recommendation from the rules engine and an accept selection control;

receiving user selection of the accept selection control in the alert user interface; and rendering in a recommendation section of the user interface page the medical best practice recommendation rendered in the alert user interface to render with the observation section and the impression section in response to receiving the user selection of the accept selection control.

6. The system of claim 5, wherein the classification program receives both the medical observation in the observation section and the classification or summary in the impression section in response to determining that the entered content in the impression section has changed.

7. The system of claim 5, wherein the operations further comprise:

storing in a log file a first fingerprint of first content entered in the impression section that uniquely identifies the first content;

generating a second fingerprint of second content entered in the impression section that uniquely identifies the second content; and determining whether the first fingerprint in the log file differs from the second fingerprint, wherein the determining that the entered content in the impression section has changed comprises determining that the first fingerprint in the log file differs from the second fingerprint.

8. A computer implemented method for processing user content entered in a user interface rendered in a computer display to obtain machine determined information, comprising:

receiving a medical observation of a patient entered by a user in a first user input field in an observation section in a user interface page to render in the observation section;

receiving content entered by the user in a second user input field in an impression section of the user interface page, comprising a classification or summary of the medical observation entered by the user in the observation section, to render in the impression section;

determining whether entered content in the impression section has changed;

in response to determining that the entered content in the impression section has changed, providing at least one of the medical observation in the observation section and the content in the impression section to a classification program, implementing a machine learning module, to classify into a machine classification comprising a medical finding based on at least one of the medical observation and the content in the impression section to provide to a rules engine, wherein the rules engine comprises a data structure that provides medical best practice recommendations for each of possible machine classifications outputted from the machine learning module, wherein the rules engine determines a medical best practice recommendation provided for the machine classification in the rules engine;

generating an alert user interface rendered with respect to the user interface page, wherein the alert user interface renders the medical best practice recommendation from the rules engine and an accept selection control;

receiving user selection of the accept selection control in the alert user interface; and rendering in a recommendation section of the user interface page the medical best practice recommendation rendered in the alert user interface to render with the observation section and the impression section in response to receiving the user selection of the accept selection control.

9. The method of claim 8, wherein the classification program receives both the medical observation in the observation section and the classification or summary in the impression section in response to determining that the entered content in the impression section has changed.

10. The method of claim 8, further comprising:

storing in a log file a first fingerprint of first content entered in the impression section that uniquely identifies the first content;

generating a second fingerprint of second content entered in the impression section that uniquely identifies the second content; and determining whether the first fingerprint in the log file differs from the second fingerprint, wherein the determining that the entered content in the impression section has changed comprises to determining that the first fingerprint in the log file differs from the second fingerprint.

* * * * *